(12) United States Patent
Accurso

(10) Patent No.: US 9,403,629 B2
(45) Date of Patent: Aug. 2, 2016

(54) KEYED CAPS FOR CONTAINERS AND DEVICES AND SYSTEMS RELATED THERETO

(71) Applicant: Abbott Laboratories, Abbott Park, IL (US)

(72) Inventor: Roger W. Accurso, Fremont, CA (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 14/137,209

(22) Filed: Dec. 20, 2013

(65) Prior Publication Data

US 2014/0263316 A1   Sep. 18, 2014

Related U.S. Application Data

(60) Provisional application No. 61/780,355, filed on Mar. 13, 2013.

(51) Int. Cl.

| | |
|---|---|
| *B01L 3/00* | (2006.01) |
| *B65D 55/14* | (2006.01) |
| *B65D 51/00* | (2006.01) |
| *B65D 51/24* | (2006.01) |
| *G01N 35/10* | (2006.01) |

(52) U.S. Cl.
CPC ................ *B65D 55/14* (2013.01); *B01L 3/523* (2013.01); *B65D 51/002* (2013.01); *B65D 51/24* (2013.01); *B01L 2200/025* (2013.01); *B01L 2300/044* (2013.01); *G01N 35/1002* (2013.01); *G01N 35/1079* (2013.01)

(58) Field of Classification Search
CPC .................. B01L 2200/025; B01L 2300/044; B01L 3/523

USPC .......................................... 422/556, 550, 568
See application file for complete search history.

(56) References Cited

U.S. PATENT DOCUMENTS

| | | | |
|---|---|---|---|
| D240,595 S | 7/1976 | Kress | |
| 4,764,342 A * | 8/1988 | Kelln et al. | ...................... 422/72 |
| 4,770,854 A * | 9/1988 | Lyman | ........................... 422/556 |

(Continued)

OTHER PUBLICATIONS

Make Your Own Gold Bars. 12' Green Gold Pan 5" #10 Mesh Screen & Bottle Snuffer—Panning Kit—Prosepecting. 2016 [online], [site visited Feb. 10, 2016]. Available from Internet, <URL:http://www.makeyourowngoldbars.com/12-green-gold-pan-5-1 0-meshscreen-bottle-snuffer-panning-kit-prospecting>.

*Primary Examiner* — Hung V Ngo
(74) *Attorney, Agent, or Firm* — Edward J. Baba; Brian E. Davy; Bozicevic, Field & Francis LLP

(57) ABSTRACT

In some aspects, a keyed cap for a container is provided. Furthermore, in some aspects, a keyed container device including a container and the keyed cap for the container is also provided. Still further, in some aspects, a keyed containing system including a container, keyed cap for the container, and an electronic device having a keying element that is adapted to mate or otherwise fit with a specific keying element on the keyed cap. If a keyed cap has a keying element that does not correctly correspond to a specific keying element on an electronic device, then the keyed cap will not properly mate with the keying element on the electronic device. For example, the two keying elements that do not match may not fit sufficiently far enough within each other to permit the piercing member on the electronic device to reach a septum on the cap.

31 Claims, 4 Drawing Sheets

(56) References Cited

U.S. PATENT DOCUMENTS

| | | | |
|---|---|---|---|
| 5,262,049 A * | 11/1993 | Ferkany | 210/258 |
| 5,413,246 A * | 5/1995 | Godolphin et al. | 222/1 |
| D363,429 S | 10/1995 | Lee | |
| 5,811,060 A * | 9/1998 | Laguna Valderrama | 422/556 |
| D419,071 S | 1/2000 | Peters | |
| 6,193,933 B1 | 2/2001 | Sasaki et al. | |
| 6,517,780 B1 * | 2/2003 | Cortelazzo | 422/557 |
| 6,599,477 B1 | 7/2003 | Miyake et al. | |
| D571,199 S | 6/2008 | Petrosino | |
| D574,708 S | 8/2008 | Reed | |
| 7,799,560 B2 * | 9/2010 | Wilson et al. | 435/297.1 |
| 8,318,111 B2 * | 11/2012 | Mingerink et al. | 422/550 |
| 8,337,780 B2 * | 12/2012 | Gaskins et al. | 422/534 |
| 8,652,424 B2 * | 2/2014 | Unger et al. | 422/556 |
| D712,739 S | 9/2014 | Lapsker | |
| D723,917 S | 3/2015 | Koffel | |
| D732,959 S | 6/2015 | Branstad | |
| 2003/0231988 A1 * | 12/2003 | Chiarin | 422/99 |
| 2004/0013575 A1 * | 1/2004 | Stevens | A61B 5/1411 422/550 |
| 2007/0246438 A1 | 10/2007 | Chen | |
| 2009/0028752 A1 * | 1/2009 | Bala | 422/58 |
| 2010/0254859 A1 * | 10/2010 | Chiarin et al. | 422/102 |
| 2012/0252134 A1 * | 10/2012 | Galiano | 436/174 |
| 2013/0045540 A1 * | 2/2013 | Collier | G01N 33/1846 436/146 |
| 2013/0209993 A1 * | 8/2013 | Aronowitz | B01L 3/5021 435/5 |
| 2014/0263316 A1 | 9/2014 | Accurso | |

\* cited by examiner

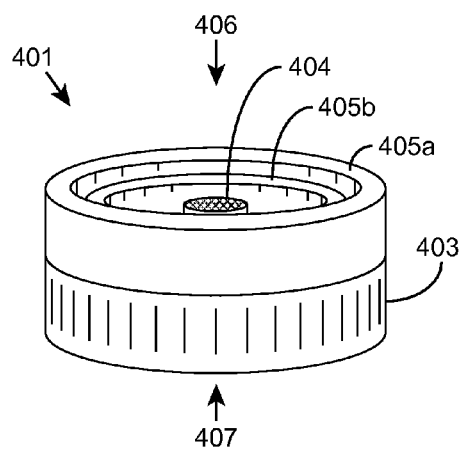
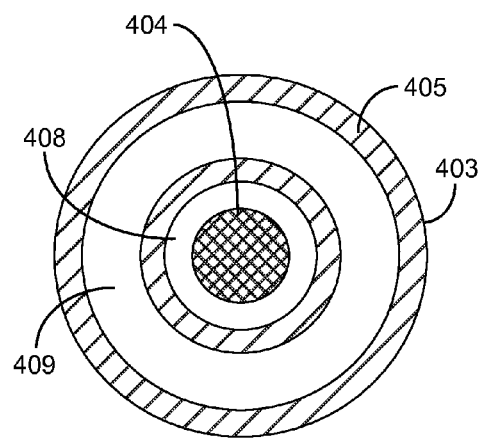
FIG. 4A
FIG. 4B
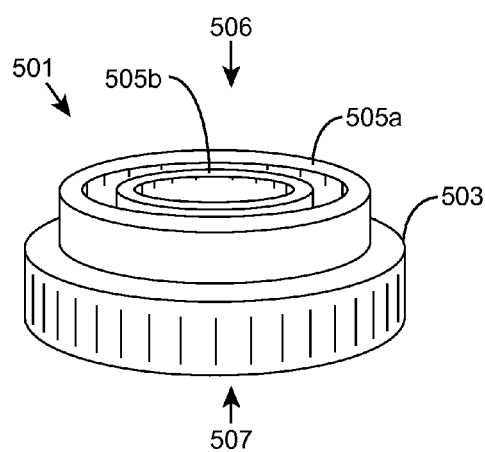
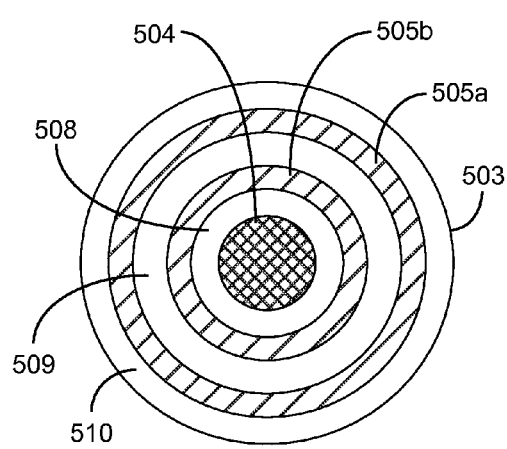
FIG. 5B
FIG. 5C

KEYED CAPS FOR CONTAINERS AND DEVICES AND SYSTEMS RELATED THERETO

CROSS-REFERENCE

This application claims the benefit of U.S. Provisional Patent Application No. 61/780,355 filed Mar. 13, 2013, which application is incorporated herein by reference in its entirety.

INTRODUCTION

Containers containing reagents are often loaded into loading ports of electronic devices to perform various testing, analysis, processing, etc., with the reagents. When loaded into the ports, a needle or piercing member is used to pierce the cap of the container to withdraw fluid for testing. Inserting containers with specific reagents into the wrong loading port, however, may lead to wasting of reagent, as well as potential cross-contamination. If cross-contamination occurs, additional steps may be required, such as flushing or otherwise decontaminating the system, which leads to wasted time and inconvenience for the user.

SUMMARY

In some aspects of the present disclosure, a keyed cap is provided. The cap includes a cap body and a septum disposed in the cap body. The cap body has a first side and a second side. The first side of the cap body is opposite the second side of the cap body. The septum has a first side and a second side. The first side of the septum is opposite the second side of the septum. Further, the first and second side of the septum faces a same direction as the first and second side of the cap body, respectively. The first side of the cap body includes a first side of the septum and a coupling element for coupling to a container. The second side of the cap body includes the second side of the septum and a keying element. The keying element includes at least one annular ring that protrudes from the second side of the cap body and that is disposed concentrically around the septum.

In some aspects of the present disclosure, a keyed containing device is provided. The keyed containing device includes a container and a cap. The container includes an opening and a first coupling element disposed around the opening. The cap includes a cap body and a septum disposed in the cap body. The cap body has a first side and a second side. The first side of the cap body is opposite the second side of the cap body. The septum has a first side and a second side. The first side of the septum is opposite the second side of the septum. Further, the first and second side of the septum faces a same direction as the first and second side of the cap body, respectively. The first side of the cap body includes a first side of the septum and a second coupling element adapted to couple with the first coupling element of the container. The second side of the cap body includes the second side of the septum and a keying element. The keying element includes at least one annular ring that protrudes from the second side of the cap body and that is disposed concentrically around the septum.

In some aspects of the present disclosure, a keyed containing system is provided that includes a container, a cap, and an electronic device. The container includes an opening and a first coupling element disposed around the opening. The cap includes a cap body and a septum disposed in the cap body. The cap body has a first side and a second side. The first side of the cap body is opposite the second side of the cap body. The septum has a first side and a second side. The first side of the septum is opposite the second side of the septum. Further, the first and second side of the septum faces a same direction as the first and second side of the cap body, respectively. The first side of the cap body includes a first side of the septum and a second coupling element adapted to couple with the first coupling element of the container. The second side of the cap body includes the second side of the septum and a first keying element. The first keying element includes at least one annular ring that protrudes from the second side of the cap body and that is disposed concentrically around the septum. The electronic device includes a second keying element adapted to mate with the first keying element of the cap, and a piercing member positioned with respect to the second keying element such that the piercing member pierces the septum of the cap when the second keying element of the electronic device is mated with the first keying element of the cap.

BRIEF DESCRIPTION OF THE FIGURES

FIGS. 4A and 4B illustrate a perspective view and top view, respectively, of keyed cap, according to yet another embodiment;

FIGS. 5B and 5C illustrate a close-up perspective view and top view, respectively, of keyed cap shown in FIG. 5A.

DETAILED DESCRIPTION

Figure 5A:
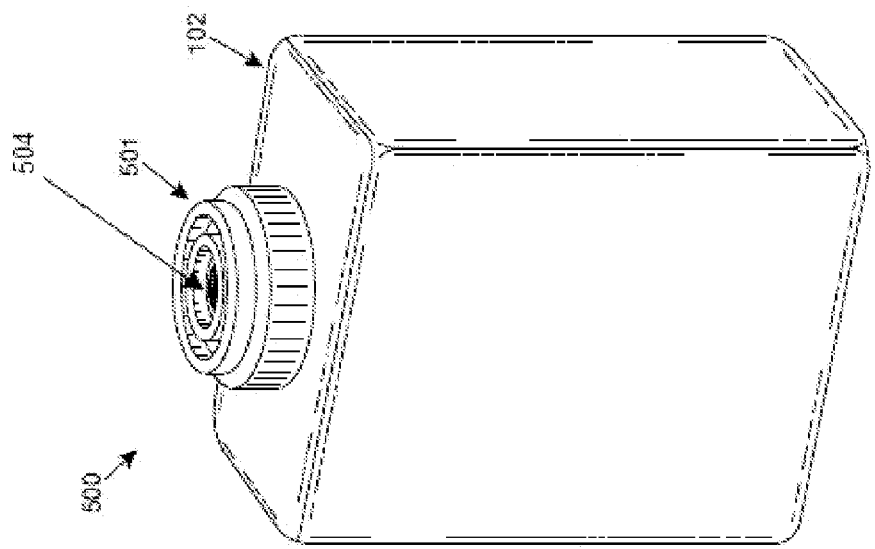
FIG. 5A illustrates a perspective view of a container device including a keyed cap and container, according to one embodiment.

In some aspects of the present disclosure, a keyed cap for a container is provided. Furthermore, in some aspects, a keyed container device including a container and the keyed cap for the container is also provided. Still further, in some aspects, a keyed containing system including a container, keyed cap for the container, and an electronic device having a keying element that is adapted to mate or otherwise fit with a specific keying element on the keyed cap. If a keyed cap has a keying element that does not correctly correspond to a specific keying element on an electronic device, then the keyed cap will not properly mate with the keying element on the electronic device. For example, the electronic device may include a piercing member that pierces the keyed cap to withdraw fluid (e.g., a reagent) when the keying elements are properly mated, but does not pierce the keyed cap when the keying elements are not properly mated. For instance, two keying elements that do not match may not fit sufficiently far enough within each other to permit the piercing member to reach a septum on the cap.

The term "septum" is used broadly herein to refer generally to a partitioning element. Any of a variety of septum types may be implemented in different embodiments. For example, a septum may be formed by, but is not limited to, membranes, fibers, a screens or mesh, valves, etc. In certain embodiments, the septum is non-permeable to fluids and able to be pierced by a piercing member (e.g., hollowed needle) such that fluid may be extracted from the container. In some instances, the septum is resealable when the piercing member is extracted from the septum, such that fluid cannot escape the container via the septum after the piercing member has been removed.

The container may vary in size and shape, and may include, for example, a known reagent bottle used to hold reagents for instance. The keyed cap may be used to prevent installing a reagent in the wrong loading port, for example, which may potentially lead to cross-contamination. As summarized above, if cross-contamination occurs, additional steps may be required, such as flushing or otherwise decontaminating the system, which leads to wasted time and inconvenience for the user.

The keyed caps include a keying element with at least one annular ring protrusion. The one or more annular rings provide a specific configuration of rings and spaces defined by the rings. The specific configuration created by the one or more annular rings functions as a "key" that requires a corresponding configuration on a receiving device (e.g., an electronic device) to enable the keying element on the cap to be received. For example, the corresponding keying element on the receiving device will be shaped and sized to properly align and receive the one or more annular rings of the keyed cap. For instance, the keying element on the receiving device may include one or more annular grooves or wells that are positioned appropriately to align with the one or more annular rings on the keyed cap. Furthermore, the keyed element on the receiving device may include one or more annular rings that are positioned appropriately to align with one more spaces on the keying element on the keyed cap that are defined by the one or more annular rings on the keyed cap.

Many annular ring configurations may be implemented in different embodiments. Accordingly, a large number of keying configurations may be implemented for keyed containers holding different reagents used by a receiving device to prevent accidental mixing-up of reagents within and between receiving devices. The receiving device may include electronic instruments, for example, that test, analyze, process, or otherwise use reagents within the keyed container. Example electronic instruments may include, but are not limited to, instruments related to hematology analysis. It should be appreciated that the electronic instruments may also include, for example, optical components that are used to perform testing, analysis, processing of the reagents, etc.

The keyed caps of the present disclosure enable a single common container to be manufactured for multiple reagents. While it is not required to use a common container, having a common container may improve manufacturability of the container and may reduce costs.

In some instances, the keyed caps may be designed with identifying characteristics or features, such as having numbers, symbols, colors, etc., that are printed or otherwise included on the keyed cap to code and identify the cap. For example, a loading area on a receiving device may include a matching color, number, or symbol, to serve as an additional aid to the user.

In certain embodiments, the keyed caps are removably coupled to the container. For example, the keyed caps may include threading which mates with threading on an opening of the container. Such threading mechanisms, or other known coupling mechanisms may be implemented to removably couple the cap and container. In certain embodiments, the keyed cap may be integrated within, or fixedly attached to, the container. For example, the keyed cap and container may be attached together with reagent inside during manufacturing. Alternatively, the keyed cap and container may include a known locking mechanism to lock the two components together when coupled.

In certain aspects, the annular rings on a keyed cap provide an additional benefit of not requiring the cap to be oriented rotationally (e.g., "clocked") to correctly mate with the receiving device. For example, other shapes such as polygons (e.g., hexagon, square, octagon, etc.) require the cap to be correctly oriented rotationally, or "clocked", to enable the cap to properly mate with the receiving device. Shapes, including annular rings, not centered around the axis of the cap may also require clocking to properly align. Furthermore, irregular shapes that are not a commonly defined shape, such as a polygon, may also require clocking. It should be appreciated that in alternative embodiments, other shapes requiring clocking may be implemented.

In certain aspects of the present disclosure, the container device including the keyed cap and the container is form fitted to a receiving port on the receiving device to enable the container device to insert within, or "plug-in" to, the port. The receiving port includes a piercing member to pierce the septum of the keyed cap when the container device is inserted within the port.

Specific ports may be adapted for use with specific reagents by having matching the keying elements in the ports with the appropriate keyed cap. Therefore, if the receiving port and the keyed cap do not have matching keying elements, then the piercing member is prevented from piercing the septum of the keyed cap and cross contamination is avoided. This provides an additional level of insurance that container devices having specific reagents are installed in the correct ports.

The cap and container may be made from any suitable material. Example materials may include, but are not limited to, polymeric materials (e.g., plastic), metals, metal alloys, or combinations thereof. The septum may be made from any suitable material that is non-permeable to fluid but enables a piercing member to pierce the septum for fluid withdrawal. For instance, any known septum be implemented.

To further describe the various aspects of the present disclosure, additional embodiments are described below. It should be appreciated that the embodiments are exemplary and that the features described may be applicable to other embodiments.

Figure 1A:
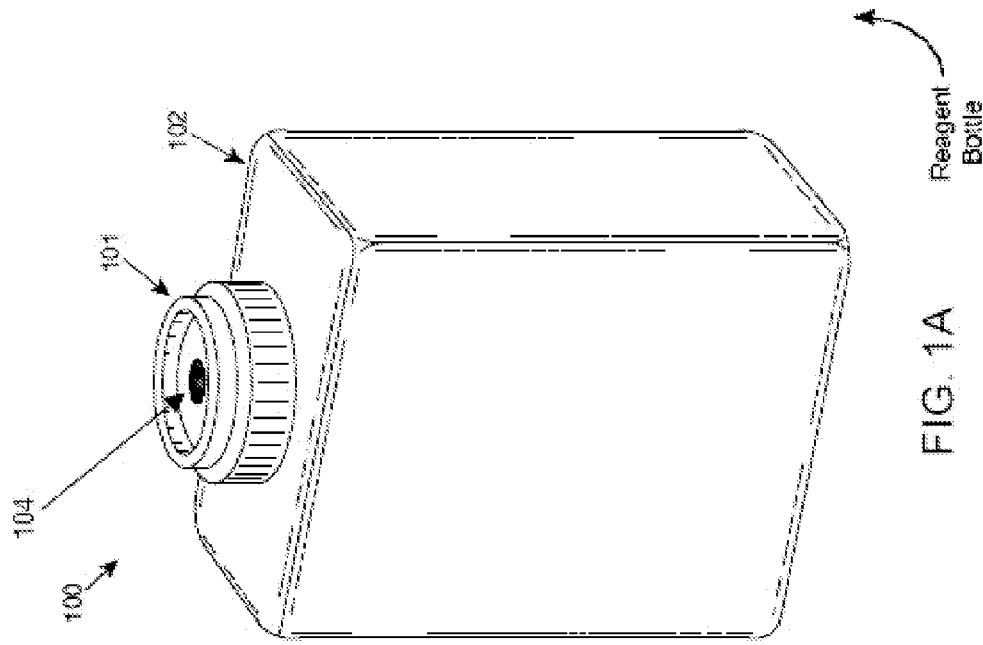
FIG. 1A illustrates a perspective view of a container device including a keyed cap and container, according to one embodiment.
Figure 1B:
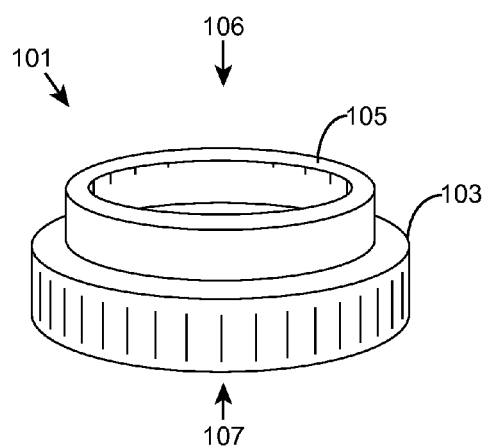
FIGS. 1B and 1C illustrates a close-up perspective view and top view, respectively, of the keyed cap shown in FIG. 1A.
Figure 1C:
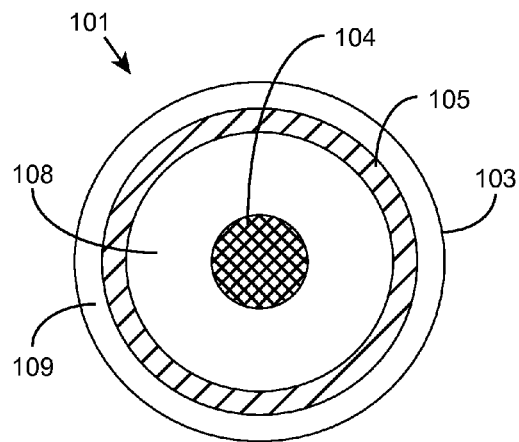

FIG. 1A illustrates a perspective view of a container device, according to one embodiment. Shown in FIG. 1A, the container device 100 includes a cap 101 and a container 102. FIGS. 1B and 1C illustrates a close-up perspective view and top view, respectively, of the cap 101 shown in FIG. 1A, and is described in conjunction with FIG. 1A.

Cap 101 is removably coupled to an opening of the container 102. For example, both the cap 101 and the container 102 may include coupling elements (not shown), such as threading, that enable the two components to be coupled together. In an alternative embodiment, the cap 101 and the container 102 may be integrated or otherwise fixedly attached to one another.

The container 102 may be made from any suitable material, but should be non-permeable to fluid. Example materials may include, but are not limited to, polymeric materials (e.g., plastic), metals, metal alloys, or combinations thereof.

The container 102 may include a coupling element (not shown) that couples to a corresponding coupling element on the cap 101. For example, the coupling element may include threading which permits the cap 101 to be screwed on and off of the container 102. Any type of coupling element may be used to couple the cap 101 to the container 102. The coupling element of the cap 101 may also include a gasket, for example, to provide an air and/or liquid tight seal when coupled.

Cap 101 is shown including a cap body 103, septum 104, and annular ring 105. Opposite sides 106,107 of cap 101 are referred to herein for reference purposes. Side 106 (e.g., the top side of cap 101) faces away from the container when cap 101 is coupled to container 102. Similarly, side 107 (e.g., the bottom side of cap 101) faces toward the container when cap 101 is coupled to the container.

The septum 104 is disposed in the cap body 103 with one side of septum 104 on side 106, and the opposite side of septum 104 on side 107. For example, side 107 of septum 104 and cap body 103 face the container 102 when coupled to the container 102. Similarly, side 106 of septum 104 and cap body 103 face away from container 102 when coupled to the container 102.

In the embodiment shown, the septum is non-permeable to fluids, but is permeable to a piercing member of a device that withdraws fluid from the container—e.g., via an inner lumen of the piercing member. It should be appreciated that in other embodiments, the size and/or shape of the septum may vary.

Cap 101 includes annular ring 105 which protrudes from side 106 of cap body 103. In the embodiment shown, the septum 104 is disposed in the center of cap body 103 with the annular ring 105 disposed concentrically around the septum 104. The annular ring 105 defines a space 108 between the annular ring 105 and the septum 104, and a space 109 between annular ring 105 and the outer perimeter cap body 103.

The annular ring 105 may vary in thickness in different embodiments. Furthermore, the spaces 108 and 109 may also vary in different embodiments. For example, as shown in FIG. 1C, the thickness of the annular ring 105 is represented as t1, with spaces 108 and 109 having widths d1 and d2, respectively.

Figure 2:
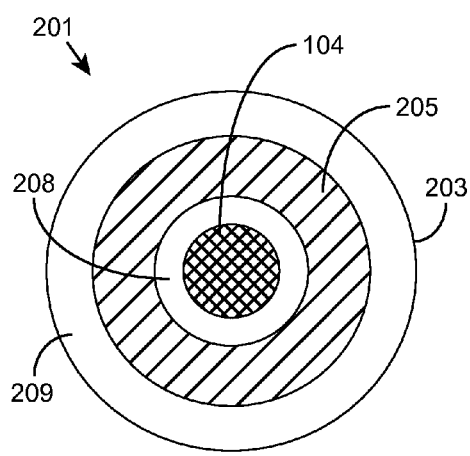
FIG. 2 illustrates a top view of keyed cap, according to another embodiment.

FIG. 2 illustrates cap 201 including a cap body 203 similar to shown in FIGS. 1A-1C, except that the annular ring 205 and spaces 5 208 and 209 differ from the from the annular ring 105 and spaces 108 and 109 shown in the embodiment shown in FIGS. 1A-1C. Annular ring 205 in FIG. 2 has a thickness, which represents a thickness greater than the thickness shown for annular ring 105 in FIGS. 1A-1C. Furthermore, spaces 208 and 209 have different widths than the widths 108 and 109, respectively. These thicknesses and widths referred to herein are measured from the inner radius to the outer radius of the corresponding ring or space—e.g., as best seen in the top-view. For instance, the width of space 208 is smaller than the width 108. It is also noted that the radial positioning of spaces may also vary independently of the widths. The term "radial positioning" is used broadly herein to represent the general distance from the center of the cap to the center of the annular ring (e.g., 205) or spaces (e.g., 208 and 209) defined by the annular ring.

Figure 3:
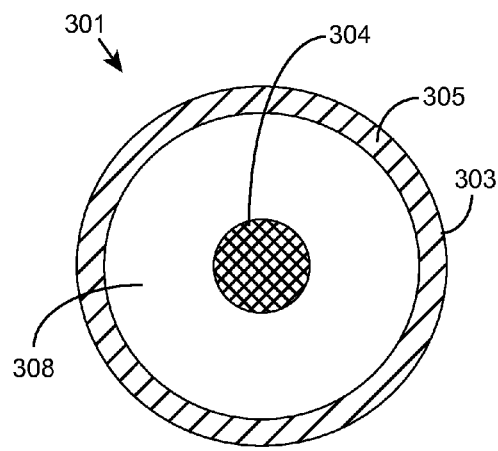
FIG. 3 illustrates a top view of a keyed cap, according to yet another embodiment.

FIG. 3 illustrates a top view of a cap according to another embodiment. Cap 301 includes a cap body 303, septum 304, and annular ring 305. One side of septum 304 is exposed and faces towards container 102 when cap 301 is coupled to container 102. The opposite side of septum 304 is exposed and faces away from container 102 when cap 301 is coupled to container 102—e.g., the side shown in the top view illustration.

Annular ring 305 protrudes from the side of cap body 303 that faces away from the container 102 when the cap 301 is coupled to the container 102—e.g., the side shown in the top view illustration.

Annular ring 305 is disposed concentrically around septum 304 at the outer perimeter of cap body 303, defining space 308 between annular ring 305 and septum 304.

It should be appreciated that the size of the keyed cap, and components within the keyed cap (e.g., annular rings, spaces defined by the annular rings, septum, etc.) may vary in different embodiments. The size of the keyed cap and components thereof may vary but should enable proper mating with the appropriately sized keying element of the receiving device. In certain embodiments, the size of the cap may range from, but is not limited to, three inches or less, such as two inches or less, and including one inch or less. In certain embodiments, the size of the annular rings may range from, but are not limited to, two centimeters or less, such as one centimeter or less, and including half a centimeter or less. In certain embodiments, the thickness of the annular rings may range depending on the size of the keyed cap being used. These example sizes are provided for exemplary purposes and should not be construed as limiting.

In certain embodiments, the cap may include more than one annular ring. For example, FIGS. 4A and 4B illustrate a perspective view and top view, respectively, of cap 401. Side 406 of cap 401 faces away from the container 102 when coupled to the container 102, and side 407 faces toward the container 102 when coupled to the container 102. Cap 401 includes a cap body 403, septum 404 exposed on both sides 406 and 407, and annular rings 405a,405b protruding from side 406 of cap body 403.

Annular ring 405a is disposed concentrically around septum 404 defining space 408 between annular ring 405a and septum 404. Annular ring 405b is disposed concentrically around both annular ring 405a and septum 404. In the embodiment shown, annular ring 405b is disposed at the outer perimeter of cap body 403 and defines a space 409 between annular ring 405a and annular ring 405b.

FIG. 5A illustrates a perspective view of a container device, according to one embodiment. Shown in FIG. 5A, the container device 500 includes a cap 501 and a container 502. FIGS. 5B and 5C illustrates a close-up perspective view and top view, respectively, of the cap 501 shown in FIG. 5A, and is described in conjunction with FIG. 5A.

Side 506 of cap 501 faces away from the container 102 when coupled to the container 102, and side 507 faces toward the container 102 when coupled to the container 102. Cap 501 includes a cap body 503, septum 504 exposed on both sides 506 and 507, and annular rings 505a,505b protruding from side 506 of cap body 503.

Annular rings 505a,505b protrude from the side of cap body 503 that faces away from the container 102 when the cap 501 is coupled to the container 102—e.g., the side shown in the top view illustration.

Annular ring 505a is disposed concentrically around septum 504 defining space 508 between annular ring 505a and septum 504. Annular ring 505b is disposed concentrically around both annular ring 505a and septum 504, defining space 509 between annular ring 505a and annular ring 505b. Annular ring 505b also defines space 510 between annular ring 505b and the outer perimeter of cap body 503.

It should be appreciated that the embodiments shown are exemplary, and that other embodiments may include more than two annular rings. It should also be appreciated that the height of each annular ring may vary in different embodiments. In certain embodiments, each annular ring has the same height. In other embodiments, two or more annular rings have different heights. For example, in the embodiment shown in FIG. 4A, annular ring 405a is greater in height than annular ring 405b. In other embodiments, such as the embodiment shown in FIG. 5B, the annular rings have the same height.

It should be appreciated that depth of each space defined by the annular rings may vary in different embodiments. The "depth" of each space is used herein to refer generally to the distance in the space from the cap body to the distal height of the annular ring. It is also understood that some spaces may be surrounded by two annular rings of different heights. In such case, the "depth" of the space may be defined based on the height of one or both annular rings—e.g., the depth of the space may be refer generally to the distance from the cap body to the distal height of either annular ring, or a combination of the two annular rings such as the middle of the two annular rings, etc. In some instances, the cap body within two spaces may differ in height from one another.

In certain embodiments, each space defined by the annular rings has the same depth. In other embodiments, two or more spaces have different depths. It should be appreciated that the base surfaces of a two spaces may be at different height levels, or alternatively may be at the same height level.

The height of the septum may also vary in different embodiments. For example, in the embodiment shown in FIG. 4A, the cap body 403 includes a raised center portion where the septum is disposed, and the septum 104 is raised to the same height as annular ring 405b. In the embodiment shown in FIG. 5B, the septum 104 is lower than the height of either of the annular rings 505a,505b. For instance, the height of the septum may be disposed at the height level where the annular rings 505a,505b meet the top surface of the cap body 503.

It is appreciated that the following parameters may vary in different embodiments: thickness and heights of the annular rings; the widths and depths of the spaces defined by the annular rings; and the radial positioning of the annular rings and spaces defined by the annular rings.

It is also appreciated that in certain embodiment, the first annular ring may be at a different height than the second annular ring, and further may be abutting the second annular ring. In such case, no space is formed between the two annular rings, however, the keying element on the receiving device may still include matching protrusions at corresponding heights to enable a "keyed" fit. It should also be appreciated that the first annular ring and the second annular ring may be made from two separate pieces or from a single piece of material molded or shaped accordingly.

Figure 6:
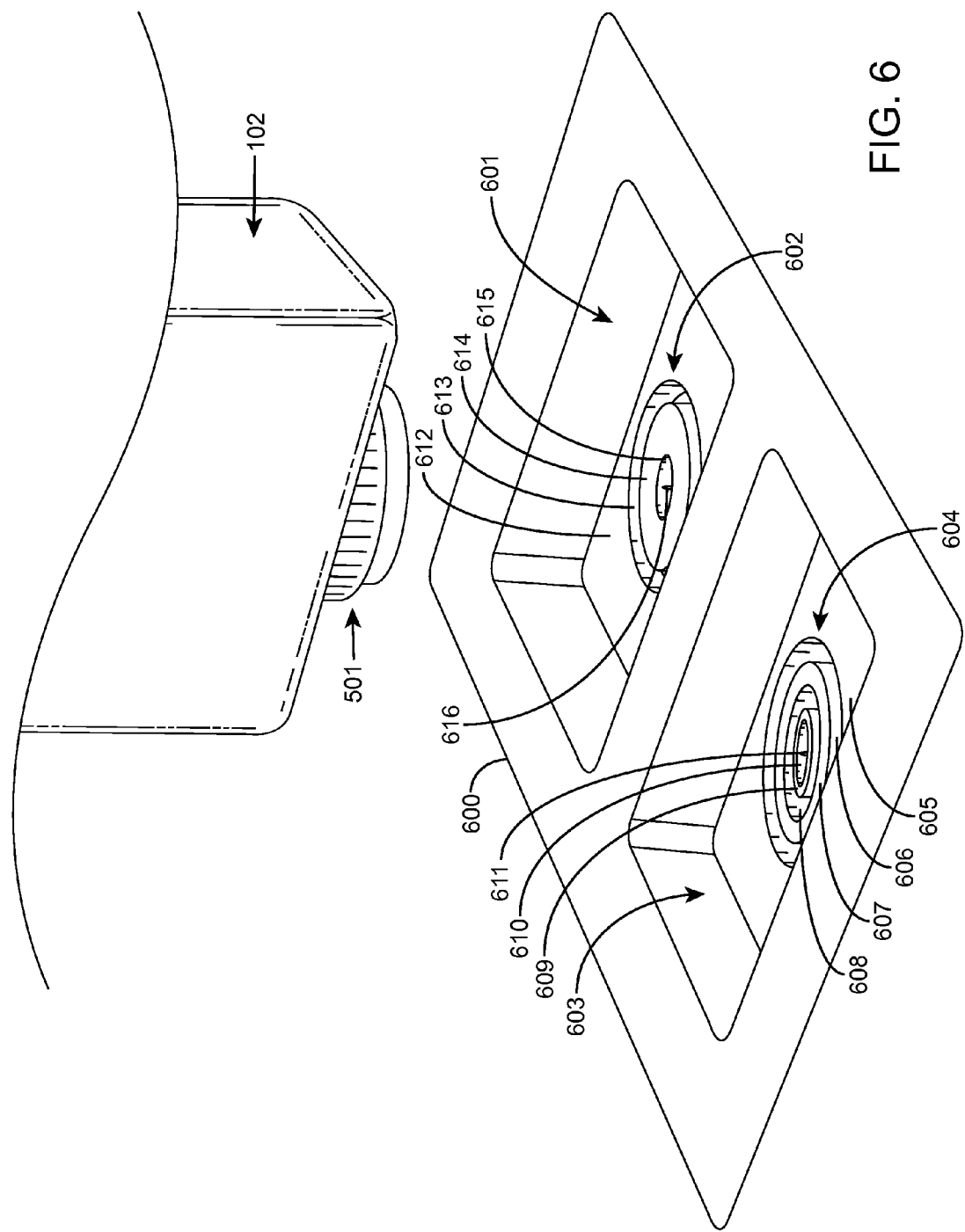
FIG. 6 illustrates a keyed containing system, according to one embodiment.

FIG. 6 illustrates a container system, according to one embodiment. The container system 600 includes a container 102 having cap 501 coupled thereto. For the embodiment shown, cap 501 is the same cap 501 as shown in FIG. 5A-5C. The container may include fluids, such as reagents for example. Container system also includes an electronic device 600 that has two ports 601,603. Port 601 includes a keying element 602 to mate with a specific annular ring configuration of a corresponding cap in which it is "keyed" to. Similarly, port 603 includes a keying element 604 that mates with a different specific annular ring configuration corresponding to a different cap.

Keying element 604 is sized and shaped to mate with cap 501. The annular rings and spaces of cap 501 form a keying element that is shaped and sized to mate with keying element 604. For example, keying element 604 includes a first annular ring 609 which aligns within space 508 of cap 501; a second annular ring 607 which aligns within space 509 of cap 501; and a portion of surface 605 that aligns with space 510 of cap 50; and a central piercing member 611 which pierces septum 504 of cap 501 when cap 501 is mated with the keying element 604. Similarly, keying element 604 includes a space 608 that aligns with annular ring 505a of cap 501; and space 606 that aligns with annular ring 505b of cap 501. Accordingly, when the containing device including the container 102 and cap 501 is brought towards port 603, the keying element 604 aligns with the protrusions and spaces of cap 501, enabling the cap 501 to fit within the keying element 604 and pierce septum 504 with the central piercing member 611.

It is appreciated that the piercing member 611 is positioned at the proper height to permit the piercing member to pierce the septum. Thus, for example, a keyed cap that does not match the keying element of the receiving element is not permitted to insert far enough to allow the piercing member to pierce the septum.

Keying element 602 of port 601 is sized and shaped to mate with different cap than 501. For example, keying element 602 is sized and shaped to mate with cap 301 shown in FIG. 3. For example, keying element 602 includes a central piercing member 616 which pierces septum 304 of cap 301; and a first annular ring 614 which aligns within space 308 of cap 301. Similarly, keying element 604 includes a space 613 that aligns with annular ring 305 of cap 301.

In FIG. 6, cap 501 includes annular rings 505a,505b and spaces 508,509,510 that form a keying element of cap 501. Keying element of cap 501 does not properly mate with the keying element 602 of port 601 because the annular rings 505a,505b and spaces 508,509,510 do not properly align with the annular ring 614 and spaces 613,615 of keyed element 602. For example, annular rings 505a,505b will contact keying element 602 but will not properly align and mate with keying element 602. Because of the improper alignment, the cap 501 is prevented from sufficient insertion to enable piercing member 616 from piercing septum 504. This provides a safety mechanism to ensure that the container is not inserted within an incorrect port, risking cross-contamination of reagents. If cross-contamination occurs, additional steps may be required, such as flushing or otherwise decontaminating the system, which causes wasted time and reagent.

Additional Example Embodiments

In some aspects of the present disclosure, a keyed cap is provided. The cap includes a cap body and a septum disposed in the cap body. The cap body has a first side and a second side. The first side of the cap body is opposite the second side of the cap body. The septum has a first side and a second side. The first side of the septum is opposite the second side of the septum. Further, the first and second side of the septum faces a same direction as the first and second side of the cap body, respectively. The first side of the cap body includes a first side of the septum and a coupling element for coupling to a container. The second side of the cap body includes the second side of the septum and a keying element. The keying element includes at least one annular ring that protrudes from the second side of the cap body and that is disposed concentrically around the septum.

In certain embodiments, the keying element comprises a first annular ring disposed between the septum and an outer perimeter of the cap body.

In certain embodiments, the keying element comprises a second annular ring. In some instances, the second annular ring is disposed between the septum and an outer perimeter of the cap body. In some instances, the keying element comprises a second annular ring disposed at an outer perimeter of the cap body. In some instances, the first annular ring and the second annular ring have different heights. In some instances, the first annular ring and the second annular ring have different thicknesses.

In certain embodiments, the keying element comprises a third annular ring. In some instances, the third annular ring is disposed between the septum and the outer perimeter of the cap body. In some instances, each of the first, second, and third annular rings have different heights. In some instances, at least two of the first, second, and third annular rings have equal heights. In some instances, each of the first, second, and third annular rings have different thicknesses. In some instances, at least two of the first, second, and third annular rings have equal thicknesses.

In some aspects of the present disclosure, a keyed containing device is provided. The keyed containing device includes a container and a cap. The container includes an opening and a first coupling element disposed around the opening. The cap includes a cap body and a septum disposed in the cap body. The cap body has a first side and a second side. The first side of the cap body is opposite the second side of the cap body. The septum has a first side and a second side. The first side of the septum is opposite the second side of the septum. Further, the first and second side of the septum faces a same direction as the first and second side of the cap body, respectively. The first side of the cap body includes a first side of the septum and a second coupling element adapted to couple with the first coupling element of the container. The second side of the cap body includes the second side of the septum and a keying element. The keying element includes at least one annular ring that protrudes from the second side of the cap body and that is disposed concentrically around the septum.

In certain embodiments, the keying element comprises a first annular ring disposed between the septum and an outer perimeter of the cap body.

In certain embodiments, the keying element comprises a second annular ring. In some instances, the second annular ring is disposed between the septum and an outer perimeter of the cap body. In some instances, the keying element comprises a second annular ring disposed at an outer perimeter of the cap body. In some instances, the first annular ring and the second annular ring have different heights. In some instances, the first annular ring and the second annular ring have different thicknesses.

In certain embodiments, the keying element comprises a third annular ring. In some instances, the third annular ring is disposed between the septum and the outer perimeter of the cap body. In some instances, each of the first, second, and third annular rings have different heights. In some instances, at least two of the first, second, and third annular rings have equal heights. In some instances, each of the first, second, and third annular rings have different thicknesses. In some instances, at least two of the first, second, and third annular rings have equal thicknesses.

In some aspects of the present disclosure, a keyed containing system is provided that includes a container, a cap, and an electronic device. The container includes an opening and a first coupling element disposed around the opening. The cap includes a cap body and a septum disposed in the cap body. The cap body has a first side and a second side. The first side of the cap body is opposite the second side of the cap body. The septum has a first side and a second side. The first side of the septum is opposite the second side of the septum. Further, the first and second side of the septum faces a same direction as the first and second side of the cap body, respectively. The first side of the cap body includes a first side of the septum and a second coupling element adapted to couple with the first coupling element of the container. The second side of the cap body includes the second side of the septum and a first keying element. The first keying element includes at least one annular ring that protrudes from the second side of the cap body and that is disposed concentrically around the septum. The electronic device includes a second keying element adapted to mate with the first keying element of the cap, and a piercing member positioned with respect to the second keying element such that the piercing member pierces the septum of the cap when the second keying element of the electronic device is mated with the first keying element of the cap.

In certain embodiments, the second keying element includes at least one annular ring positioned to align with spaces defined by at least one annular ring of the first keying element.

In certain embodiments, the second keying element includes at least one space defined by an annular ring, the at least one space of the second keying element positioned to align with at least one annular ring of the first keying element.

In certain embodiments, the first keying element comprises a first annular ring disposed between the septum and an outer perimeter of the cap body.

In certain embodiments, the first keying element comprises a second annular ring. In some instances, the second annular ring of the first keying element is disposed between the septum and an outer perimeter of the cap body. In some instances, the first keying element comprises a second annular ring disposed at an outer perimeter of the cap body. In some instances, the first annular ring and the second annular ring of the first keying element have different heights. In some instances, the first annular ring and the second annular ring of the first keying element have different thicknesses.

In certain embodiments, the first keying element comprises a third annular ring. In some instances, the third annular ring of the first keying element is disposed between the septum and the outer perimeter of the cap body. In some instances, each of the first, second, and third annular rings of the first keying element have different heights. In some instances, at least two of the first, second, and third annular rings of the first keying element have equal heights. In some instances, each of the first, second, and third annular rings of the first keying element have different thicknesses. In some instances, at least two of the first, second, and third annular rings of the first keying element have equal thicknesses.

In some aspects of the present disclosure, an electronic device is provided that includes a keying element adapted to mate with another keying element of a keyed cap according to the present disclosure. The electronic device includes a piercing member positioned with respect to the keying element of the electronic device, such that the piercing member pierces the septum of the keyed cap when the keying element of the electronic device is mated with the first keying element of the cap.

In certain embodiments, the keying element of the electronic device includes at least one annular ring positioned to align with spaces defined by at least one annular ring of the keying element of the keyed cap.

In certain embodiments, the keying element of the electronic device includes at least one space defined by an annular ring, the at least one space of the keying element of the electronic device is positioned to align with at least one annular ring of the keying element of the keyed cap.

Although the foregoing embodiments have been described in some detail by way of illustration and example for purposes of clarity of understanding, it is readily apparent to those of ordinary skill in the art in light of the teachings of the present disclosure that certain changes and modifications may be made thereto without departing from the spirit or scope of the appended claims. It is also to be understood that the terminology used herein is for the purpose of describing particular embodiments only, and is not intended to be limiting.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein.

The invention claimed is:

1. A keyed containing system, comprising:
    a container, the container comprising:
        an opening; and
        a first coupling element disposed around the opening; and
    a cap, the cap comprising:
        a cap body comprising a first side comprising a first surface and a second side comprising a second surface, wherein the first side of the cap body is opposite the second side of the cap body and the first surface is opposite the second surface; and
        a septum disposed in the cap body, wherein the septum has a first material and has a first side and a second side, wherein the first side of the septum is opposite the second side of the septum, and wherein the first and second side of the septum face a same direction as the first and second side of the cap body, respectively;
        wherein a first side of the cap body comprises:
            the first side of the septum; and
            a second coupling element adapted to couple with the first coupling element of the container;
        wherein the second side of the cap body comprises:
            the second side of the septum; and
            a keying element, wherein the keying element comprises at least one annular ring protruding from the second side of the cap body and defining on the second surface a first space between the annular ring and the septum, and a second space between the annular ring and an outer perimeter of the cap body, wherein the at least one annular ring is disposed concentrically around the septum, and wherein the at least one annular ring is comprises of a second material that is different from the first material; and
    a device comprising a keying element adapted to mate with the keying element of the cap.

2. The keyed containing device of claim 1, wherein the keying element comprises a first annular ring disposed between the septum and an outer perimeter of the cap body.

3. The keyed containing device of claim 1, wherein the keying element comprises a second annular ring.

4. The keyed containing device of claim 3, wherein the second annular ring is disposed between the septum and an outer perimeter of the cap body.

5. The keyed containing device of claim 3, wherein the keying element comprises a second annular ring disposed at an outer perimeter of the cap body.

6. The keyed containing device of claim 3, wherein the first annular ring and the second annular ring have different heights.

7. The keyed containing device of claim 3, wherein the first annular ring and the second annular ring have different thicknesses.

8. The keyed containing device of claim 3, wherein the keying element comprises a third annular ring.

9. The keyed containing device of claim 8, wherein the third annular ring is disposed between the septum and the outer perimeter of the cap body.

10. The keyed containing device of claim 8, wherein each of the first, second, and third annular rings have different heights.

11. The keyed containing device of claim 8, wherein at least two of the first, second, and third annular rings have equal heights.

12. The keyed containing device of claim 8, wherein each of the first, second, and third annular rings have different thicknesses.

13. The keyed containing device of claim 8, wherein at least two of the first, second, and third annular rings have equal thicknesses.

14. The keyed containing device according to claim 1, wherein an inner diameter of the annular ring is greater than an outer diameter of the spectrum.

15. A keyed containing system, comprising:
a container, the container comprising:
an opening; and
a first coupling element disposed around the opening; and
a cap, the cap comprising:
a cap body having a first side and a second side, wherein the first side of the cap body is opposite the second side of the cap body; and
a septum disposed in the cap body, wherein the septum has a first side and a second side, wherein the first side of the septum is opposite the second side of the septum, and wherein the first and second side of the septum faces a same direction as the first and second side of the cap body, respectively;
wherein a first side of the cap body comprises:
the first side of the septum; and
a second coupling element adapted to couple with the first coupling element of the container;
wherein the second side of the cap body comprises:
the second side of the septum; and
a first keying element, wherein the first keying element comprises at least one annular ring protruding from the second side of the cap body, wherein the at least one annular ring is disposed concentrically around the septum; and
an electronic device, the electronic device comprising:
a second keying element adapted to mate with the first keying element of the cap; and
a piercing member positioned with respect to the second keying element such that the piercing member pierces the septum of the cap when the second keying element of the electronic device is mated with the first keying element of the cap.

16. The keyed containing system of claim 15, wherein the second keying element includes at least one annular ring positioned to align with spaces defined by at least one annular ring of the first keying element.

17. The keyed containing system of claim 15, wherein the second keying element includes at least one space defined by an annular ring, the at least one space of the second keying element positioned to align with at least one annular ring of the first keying element.

18. The keyed containing system of claim 15, wherein the first keying element comprises a first annular ring disposed between the septum and an outer perimeter of the cap body.

19. The keyed containing system of claim 15, wherein the first keying element comprises a second annular ring.

20. The keyed containing system of claim 19, wherein the second annular ring of the first keying element is disposed between the septum and an outer perimeter of the cap body.

21. The keyed containing system of claim 19, wherein the first keying element comprises a second annular ring disposed at an outer perimeter of the cap body.

22. The keyed containing system of claim 19, wherein the first annular ring and the second annular ring of the first keying element have different heights.

23. The keyed containing system of claim 19, wherein the first annular ring and the second annular ring of the first keying element have different thicknesses.

24. The keyed containing system of claim 19, wherein the first keying element comprises a third annular ring.

25. The keyed containing system of claim 24, wherein the third annular ring of the first keying element is disposed between the septum and the outer perimeter of the cap body.

26. The keyed containing system of claim 24, wherein each of the first, second, and third annular rings of the first keying element have different heights.

27. The keyed containing system of claim 24, wherein at least two of the first, second, and third annular rings of the first keying element have equal heights.

28. The keyed containing system of claim 24, wherein each of the first, second, and third annular rings of the first keying element have different thicknesses.

29. The keyed containing system of claim 24, wherein at least two of the first, second, and third annular rings of the first keying element have equal thicknesses.

30. The keyed containing system of claim 15, wherein the first side of the cap body comprises a first surface, wherein the second side of the cap body comprises a second surface opposite the first surface, and wherein the at least one annular ring of the first keying element protrudes orthogonally from the second surface.

31. The keyed containing system of claim 15, wherein the first side of the cap body comprises a first surface, wherein the second side of the cap body comprises a second surface opposite the first surface, and wherein the at least one annular ring of the first keying element defines on the second surface a first space between the annular ring and the septum, and a second space between the annular ring and an outer perimeter of the cap body.

* * * * *